United States Patent [19]
Soe et al.

[11] Patent Number: 5,888,749
[45] Date of Patent: Mar. 30, 1999

[54] ANTI-HUMAN PLASMIN-$\alpha_2$-PLASMIN INHIBITOR COMPLEX ANTIBODIES, HYBRIDOMAS, AND IMMUNOLOGICAL DETERMINATION METHOD

[75] Inventors: Gilbu Soe; Isao Kohno; Mami Shiiba, all of Tokyo, Japan

[73] Assignee: Iatron Laboratories, Inc., Tokyo, Japan

[21] Appl. No.: 920,544

[22] PCT Filed: Dec. 19, 1991

[86] PCT No.: PCT/JP91/01736

§ 371 Date: Sep. 21, 1992

§ 102(e) Date: Sep. 21, 1992

[87] PCT Pub. No.: WO92/11384

PCT Pub. Date: Jul. 9, 1992

[30] Foreign Application Priority Data

Dec. 20, 1990 [JP] Japan .................................. 2-411805

[51] Int. Cl.$^6$ ..................... G01N 33/573; G01N 33/546; C07K 16/36
[52] U.S. Cl. ............................. 435/7.4; 435/13; 436/518; 436/523; 436/528; 436/531; 436/534; 530/388.25
[58] Field of Search .................................... 436/518, 523, 436/528, 531, 533, 69, 540, 534; 435/13, 7.4, 7.92, 7.94; 530/388.25

[56] References Cited

U.S. PATENT DOCUMENTS

| | | |
|---|---|---|
| 4,216,291 | 8/1980 | Collen . |
| 4,618,589 | 10/1986 | Jefferis et al. ........................... 436/540 |
| 4,629,694 | 12/1986 | Harpel . |
| 4,820,635 | 4/1989 | Sanders et al. . |
| 4,840,895 | 6/1989 | Self ..................................... 436/518 X |
| 4,849,353 | 7/1989 | Harpel ..................................... 435/7.4 |
| 5,587,291 | 12/1996 | Binder . |

FOREIGN PATENT DOCUMENTS 0169549  1/1986  European Pat. Off. ................. 435/13

OTHER PUBLICATIONS

Collen, et al. Biochemica et Biophysica Acta, 525 (1978), 287–290.

Pelzer, et al., Thrombosis and Haemostasis, Abstract 2061.

S. Gonias et al. *The Journal of Biological Chemistry*, vol. 263, No. 22 5 Aug. 1988, pp. 10903–10906.

P. Harpel et al, *Journal of Clinical Investigation*, vol 68, Jul. 1981 pp. 46–55.

M. Kawakami et al, *Arthritis and Rheumatism*, vol. 32, No. 11, Nov. 1989, pp. 1427–1432.

H. Plow et al, *Journal of Laboratory Clinical Medicine*, Feb. 1979, pp. 199–209.

Lerch et al., "Localization of Individual Lysine–Binding Regions in Human Plasminogen and Investigations on Their Complex–Forming Properties", *Eur. J. Biochem.*, vol. 107, pp. 7–13, (1980).

Hochschwender et al., "Immunochemical Characterization of the Kringle 4 Fragment of Human Plasminogen", *The Journal of Biological Chemistry*, , vol. 256, No. 21, (1981), pp. 11166–11171.

Pelzer et al., "Determination of $\alpha_2$–antiplasmin–plasmin Complex in Human Plasma with an Enzyme–linked Immunosorbent Assay", *Fibrinolysis*, vol. 7, (1993), pp. 69–74.

(List continued on next page.)

*Primary Examiner*—Susan Wolski
*Attorney, Agent, or Firm*—Sherman and Shalloway

[57] ABSTRACT

A first monoclonal antibody which specifically reacts with a human $\alpha_2$-plasmin inhibitor complex (PIC) and a human plasminogen; a second monoclonal antibody which reacts with PIC and also with a human $\alpha_2$-plasmin inhibitor; a third monoclonal antibody which reacts with PIC, but does not react with a human plasminogen and a human $\alpha_2$-plasmin inhibitor; hybridomas which secrete the first to third monoclonal antibodies, and an immunoassay using the first to third monoclonal antibodies.

29 Claims, 1 Drawing Sheet

OTHER PUBLICATIONS

Holvoet et al., "A Monoclonal Antibody Specific for Lys–plasminogen", *The Journal of Biological Chemistry*, vol. 262, No. 22, (1985), pp. 12106–12111.

Hosoda et al., "Homogeneous immunoassay for $\alpha_2$ plasmin inhibitor ($\alpha_2$Pl) and $\alpha_2$Pl–plasmin complex", *Journal of Immunological Methods*, vol. 121, (1989), pp. 121–128.

Mimuro et al., "Monoclonal Antibodies to Discrete Regions in $\alpha_2$–Plasmin Inhibitor", *Blood*, vol. 69, No. 2, (1987), pp. 446–453.

Asakura et al., "Preparation and characterization of monoclonal antibodies against the human thrombin–antithrombin III complex", *Biochimica et Biophysica Acta*, vol. 952, (1988), pp. 37–47.

Ploplis et al., "Monoclonal Antibodies to Discrete Regions of Human $Glu_1$–Plasminogen", *Biochemistry*, vol. 21, (1982), pp. 5891–5897.

Cummings et al., "Imterspecies Cross–Reactivity of Monoclonal Antibodies to Various Epitopes of Human Plasminogen", vol. 230, No. 1, (1984), pp. 306–315.

Miles et al., "Topography of the High–Affinity Lysine Binding Site of Plasminogen As Defined with a Specific Antibody Probe", *Biochemixtry*, vol. 25, (1986), pp. 6926–6933.

ANTI-HUMAN PLASMIN-$\alpha_2$-PLASMIN INHIBITOR COMPLEX ANTIBODIES, HYBRIDOMAS, AND IMMUNOLOGICAL DETERMINATION METHOD This application is a 371 of PCT/JP91/01736, filed Dec. 19, 1991.

TECHNICAL FIELD

The present invention relates to a group of various types of monoclonal antibodies having reactivity with a human plasmin-$\alpha_2$-plasmin inhibitor complex (hereinafter optionally referred to as "PIC"), various types of hybridomas secreting the above monoclonal antibodies, and a method for immunologically determining a human plasmin-$\alpha_2$-plasmin inhibitor complex using the above monoclonal antibodies.

BACKGROUND ART

In the plasma of patients suffering from disseminated intravascular coagulation (DIC) and in the plasma of patients being treated by the thrombolytic therapy using urokinase or tissue plasminogen activators (t-PA), a plasminogen is activated to produce a plasmin. The resulting plasmin immediately forms a complex with an $\alpha_2$-plasmin inhibitor ($\alpha_2$PI: Aoki et al., J. Biol. Chem., 251, 5956–5965, 1976) at a ratio of 1:1 in circulating blood. The complex is the above PIC. Therefore, by measuring the PIC, it is possible to detect the activation of the plasmin. Recently, the PIC in the plasma is considered important in the diagnosis of DIC, as a molecular marker for monitoring the thrombolytic therapy, and so on. Accordingly, it is necessary to accurately and simply measure the amount of PIC in the blood or plasma.

As conventionally known methods for measuring PIC, there may be mentioned the following five methods. The first method uses two-dimensional crossed immunoelectrophoresis. The second method is a latex agglutination using polyclonal antibodies which recognize the necantigen of PIC. The third method is an enzyme immunoassay wherein a polyclonal antibody against the plasminogen and a polyclonal antibody against the $\alpha_2$-plasmin inhibitor, and one of them is immobilized and the other is labelled by an enzyme. The fourth method is an enzyme immunoassay wherein a monoclonal antibody which specifically recognizes the sites inhibiting the fibrinolysis action of the plasmin and existing in the $\alpha_2$-plasmin inhibitor, and a polyclonal antibody against a plasmin are used; one of them is immobilized and the other is labelled by an enzyme; and the plasma specimen is diluted 1200-fold for measurement. The fifth method is the latex agglutination wherein two or three types of monoclonal antibodies which recognize the necantigen of PIC are used.

The first method, however, had the defects of a low sensitivity and lack of quantitativeness. The second method had the defects that the PIC cannot be specifically measured. The third method had the defects that, while the sensitivity is good, it is difficult to stably obtain anti-serum; and the immunoreaction is a two-step process, and so the procedure is complicated to require a long time for the measurement. In the fourth method, the defects of the third method were remedied by using a monoclonal antibody against the $\alpha_2$-plasmin inhibitor and carrying out the immunoreaction in a single step. However, the fourth method did not solve the defects inherent to the enzyme immunoreaction, that is, the complicated procedure and the long time required for the measurement. Further, the fourth method had the defects that it required the step of diluting the specimen 1200-fold so as to enable the single-step immunoreaction. The fifth method did not exhibit different specificity and measuring sensitivity in comparison with those of the second method wherein a polyclonal antibody is used, and did not solve the problem of the inability of specifically measuring PIC.

The present inventors engaged in research to develop a method for simply and accurately measuring PIC with good reproducibility, and as a result discovered three types of monoclonal antibodies; a first monoclonal antibody (PIC-1) exhibiting reactivity with both PIC and a plasminogen, a second monoclonal antibody (PIC-2) exhibiting reactivity with both PIC and an $\alpha_2$-plasmin inhibitor, and a third monoclonal antibody (PIC-3) exhibiting specific reactivity with PIC, but not exhibiting reactivity with a plasminogen and an $\alpha_2$-plasmin inhibitor which are the component proteins of the PIC, and further discovered that when a combination of two or more of these monoclonal antibodies are used, it is possible to specifically determine rapidly and accurately the PIC in the plasma without a step of dilution of the plasma specimen and without suffering from the interference of a free plasminogen and a free $\alpha_2$-plasmin inhibitor present in the specimen. Therefore, the object of the present invention is to provide the above-mentioned novel monoclonal antibodies, hybridomas producing the above monoclonal antibodies, and an immunological determination method using the monoclonal antibodies.

DISCLOSURE OF THE INVENTION

Accordingly, the present invention relates to
(1) a first monoclonal antibody which specifically reacts with a human plasmin-$\alpha_2$-plasmin inhibitor complex and a human plasminogen;
(2) a second monoclonal antibody which specifically reacts with a human plasmin-$\alpha_2$-plasmin inhibitor complex and a human $\alpha_2$-plasmin inhibitor; and
(3) a third monoclonal antibody which specifically reacts with a human plasmin-$\alpha_2$-plasmin inhibitor complex, but does not react with a human plasminogen and a human $\alpha_2$-plasmin inhibitor.

Further, the present invention relates to hybridomas which secrete the first to third monoclonal antibodies and cell lines thereof.

Further, the present invention relates to a method for determining a human plasmin-$_2$-plasmin inhibitor complex characterized by bringing at least two of the above first to third monoclonal antibodies immobilized on an insoluble carrier, into contact with a sample; and observing an agglutination reaction in the sample.

BEST MODE FOR CARRYING OUT THE INVENTION

Figure 1:
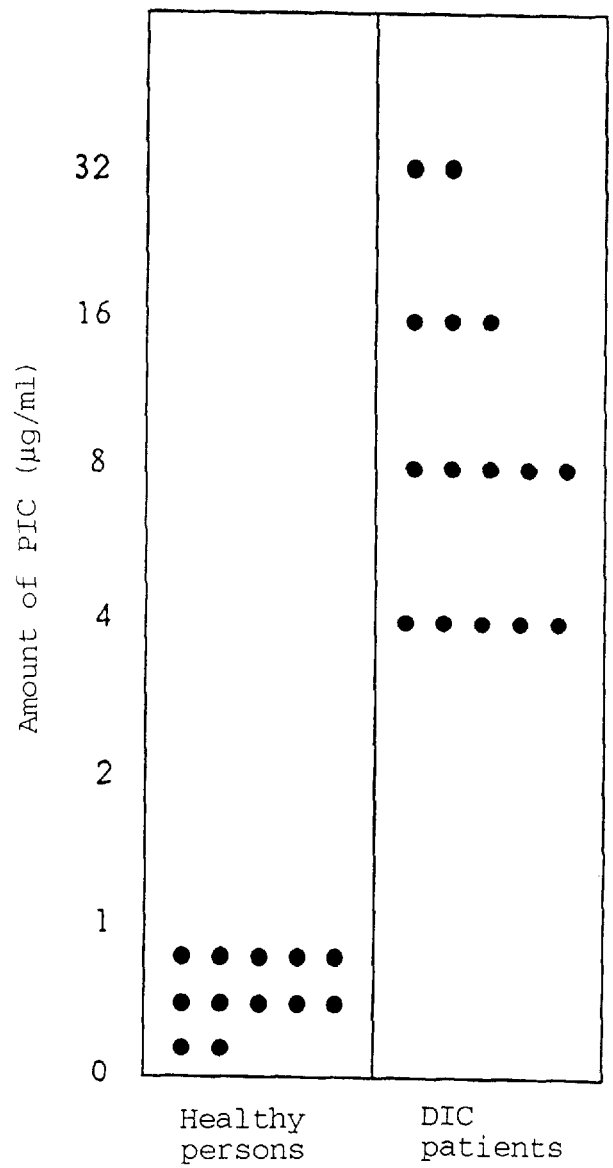
FIG. 1 shows the results of measurement of the amounts of PIC in the plasma of healthy persons (12 specimens) and the plasma of DIC patients (15 specimens), using the monoclonal antibody-latex complex according to the present invention.

The present invention will be explained hereinafter in the order of the monoclonal antibodies, the hybridomas, and the immunological determination method.

The PIC used as the immunogen may be prepared in accordance with, for example, the method of Plow et al. (J. Lab. Clin. Med. 93, 199–209, 1979). Namely, the plasminogen is removed from the plasma of a healthy person. To the resulting plasma without the plasminogen, a plasmin is gradually added to produce PIC therein, and then the produced PIC is absorbed in a suitable affinity gel. The absorbed PIC is eluted with a suitable buffer solution and is treated by a purification procedure using ion exchange chromatography, molecular sieve chromatography, or the like to obtain the purified human PIC. The resulting human PIC exhibits a single band under SDS-PAGE (SDS-Polyacrylamidegel electrophoresis).

Then, the immunogen solution of the purified PIC is used to immunize mammals (for example, mice, rats, rabbits, goats, and horses) by the in-vivo immunization method.

More particularly, for example, the purified human PIC immunogen solution is mixed with an equal amount of complete Freund's adjuvant or incomplete adjuvant until emulsified. The mixture is administered, for example, subcutaneously to mice (a first immunization). Then, the same procedure is repeated at intervals of two to four weeks for several immunizations. The spleens are removed aseptically several days after the final immunization, and crushed by a stainless steel mesh or the like to prepare the spleen cells which are used for the cell fusion.

As the other parent cells used for the cell fusion, that is, the myeloma cells, there may be used various types of known cell lines, such as, p3 (p3/x63-Ag8) [Nature, 256, 495–497 (1975), p3-U1 [Current Topics in Microbiology and Immunology, 81; 1–7 (1978)], NS-1 [Eur. J. Immunol., 6; 511–519 (1976)], MPC-11 [Cell, 8; 405–415 (1976)], SP2/0 [Nature, 276; 269–270 (1978)], FO [J. Immunol. Meth., 35; 1–21 (1980)], x63.6.55.3 [J. Immunol., 123; 1548–1550 (1979)], S194 [J. Exp. Med., 148; 313–323 (1978)], R210 from rats [Nature, 277; 131–133 (1979)], or the like.

The cell fusion between the immune spleen cells and myeloma cells may be carried out by ordinary methods. For example, a known fusion promotor (polyethylene glycol, Sendai virus, or the like) and optionally an auxiliary agent (dimethyl sulfoxide or the like) may be used. The ratio of the immune spleen cells and myeloma cells may be the same as in ordinary methods. For example, spleen cells may be used in amounts about one to 10 times the amount of the myeloma cells. As the fusion medium, for example, the Dulbecco modified Eagle's medium (DMEM) containing 40 percent (w/v) polyethyleneglycol may be used. The fusion is carried out by thoroughly mixing the immunized spleen cells and myeloma cells in the above medium. Then, a selecting medium (for example, HAT medium) is used to remove the cells other than the hybridoma. The target hybridomas are separated by detecting the presence of the antibodies produced in the supernatant of the hybridoma cultivation by, for example, the ELISA method.

The obtained hybridoma PIC-1, PIC-2 and PIC-3 secreting the monoclonal antibodies PIC-1, PIC-2 and PIC-3 of the present invention can be successively cultured in ordinary media, and can be easily stored for long periods in liquid nitrogen or the like.

As the medium for cultivating the hybridomas, any medium suitable for cultivation of a hybridoma may be used. Preferably, a medium comprising the DMEM including fetal calf serum, L-glutamin, L-pyruvic acid and antibiotics (penicillin G and streptomycin) is used.

The cultivation of the hybridoma is preferably carried out for example in a medium at a 5 percent $CO_2$ concentration and 37° C. for about three days in the case of in vitro cultivation, or for about 14 days in the case of in vivo cultivation, for example, in the abdominal cavities of mice.

The target monoclonal antibodies may be separated and purified from the cultivation liquid obtained by cultivating the hybridoma PIC-1, PIC-2 or PIC-3 by an ordinary method, or from the ascites of suitable mammals (for example, mice or rats) administered with one of the three hybridomas.

When separating and purifying the monoclonal antibodies from the thus prepared cultivation liquid or mouse ascites, it is possible to use the method generally applied for the isolation and purification of proteins. As examples thereof, there may be mentioned the ammonium sulfate salting out, ion exchange chromatography, molecular sieve chromatography using molecular sieve gel, affinity column chromatography using protein A binding polysaccharides, dialysis, lyophilization, or the like. The resulting anti-PIC monoclonal antibodies of the present invention can be classified into the following three types by their reactivities:

(1) A first monoclonal antibody (PIC-1) which reacts with PIC and a plasminogen, but does not react with an $\alpha_2$-plasmin inhibitor.
(2) A second monoclonal antibody (PIC-2) which reacts with PIC and an $\alpha_2$-plasmin inhibitor, but does not react with a plasminogen.
(3) A third monoclonal antibody (PIC-3) which reacts with PIC, but does not react with a plasminogen and an $\alpha_2$-plasmin inhibitor.

The first monoclonal antibody (PIC-1) preferably recognizes the region including the Kringle 2 and Kringle 3 of the human plasminogen.

If the first to third anti-PIC monoclonal antibodies according to the present invention are immobilized on insoluble carriers and at least two of the same are brought into contact with a specimen, it is possible to cause an agglutination reaction only with the PIC, while no agglutination reaction is caused with the free plasminogen and $\alpha_2$-plasmin inhibitor in the specimen. Therefore, the antibodies may be used for a method for immunologically determining PIC, and are useful also as a reagent for immunoassay.

The specimen used for the immunoassay method of the present invention is not particularly limited, so long as it has a possibility to include PIC. Examples thereof are physiological samples, in particular blood, serum, and plasma, or urine, in particular plasma. In the method of immunoassay method of the present invention, it is possible to avoid interference of the plasminogen and $\alpha_2$-plasmin inhibitor present in a free state in the specimen, even when the specimen is directly used without dilution. Namely, according to the method of the present invention, it is possible to determine a human plasmin-$\alpha_2$-plasmin inhibitor complex without suffering from the interference of the plasminogen and $\alpha_2$-plasmin inhibitor present in the specimen.

The insoluble carrier which may be used in the present invention is any insoluble carrier which is generally used in the immunological determination methods using the agglutination reaction between antigens and antibodies, for example, latex particles (in particular, polystyrene latex particles).

To immobilize the monoclonal antibodies of the present invention on the insoluble carrier, known methods, such as the chemical bonding method (using carbodiimide, glutaraldehyde, or the like as the cross-linking agent) or physical absorption method may be used. Thus, a complex of the monoclonal antibody and the insoluble carrier may be produced and used for the immunoassay method of the present invention.

In the immunoassay method of the present invention, at least two of the monoclonal antibodies immobilized on the above insoluble carrier are used. It is possible to use two or three types of complexes prepared by immobilizing each of the monoclonal antibodies on an insoluble carrier, respectively, or to use a complex prepared by immobilizing two or three types of monoclonal antibodies on an insoluble carrier. Further, it is possible to use a combination of one type of complex prepared by immobilizing one type of monoclonal antibody on an insoluble carrier and one type of complex prepared by immobilizing two types of monoclonal antibodies on an insoluble carrier. Any combination of two types of monoclonal antibodies of the present invention may be used, but it is preferable to use a combination of the first monoclonal antibody (PIC-1) and the second monoclonal antibody (PIC-2).

In the determination method of the present invention, a known predetermined amount of the above monoclonal antibody immobilizing insoluble carrier complex and a predetermined amount of an aqueous sample containing an unknown amount of PIC are brought into contact in a suitable reaction vessel (for example, on a slide plate or reaction cell). For example, in the case of a plasma specimen, one part by volume or more than one part by volume of the above-mentioned complex suspension having a concentration of at least 1% was added to and brought into contact with one part by volume of a plasma specimen (undiluted liquid). To obtain more clear agglutination, it is possible to add a buffer solution (for example, a tris hydrochloride buffer solution) to the specimen and the complex suspension and bring it into contact therewith. The concentration of the PIC can be determined from the extent of the agglutination formed in the above manner. Defection of the agglutination reaction is not inhibited by free plasminogen and $\alpha_2$-plasmin inhibitor present in the plasma specimens. For example, the agglutination reaction can be measured visually in the case of a slide plate, or spectroscopically using a specific wavelength in the case of a reaction cell, to determine the concentration of PIC in the specimen.

EXAMPLES

The present invention now will be further illustrated by, but by no means limited to, the following Examples.

Example 1

Preparation of Hybridomas (a) Purification of PIC

A human plasma-$\alpha_2$-plasmin inhibitor complex (PIC) was purified in accordance with the method of Plow et al. (J. Lab. Clin. Med. 93, 199–209, 1979). A brief explanation thereof will be given hereinafter. Human (healthy person) plasma (100 ml) was passed through a lysine-Sepharose column (bed capacity=100 ml) to remove the plasminogen. To the resulting plasma without plasminogen, 100 ml of an aqueous solution of plasmin (60 µg/ml) was gradually added. Then, the whole was held at 37° C. for 10 minutes. The aqueous reaction solution was passed through a lysine-Sepharose™ (ion exchange beads) column (bed capacity=200 ml) to absorb the PIC. Sepharose™ is a bead carrier made of agarose. The PIC absorbing column was washed by 0.1M phosphate buffered s ine (PBS), and the PIC was eluted by PBS including 50 mM ε-aminocaproic acid.

Further, the resulting PIC was purified by molecular sieve chromatography using ULTROGEL ACA44 (a mixed matrix of polyacrylamide and agarose) for size exclusion. The purified PIC was used in the screening of the immunogens and anti-PIC monoclonal antibodies.

(b) Preparation of Immunized Spleen Cells

The PIC immunogen solution (A280 nm=0.1) was mixed with an equal amount of complete Freund's adjuvant until emulsified, then 200 µl of the mixture was administered intraperitoneally in BALB/c mice to immunize the same (first immunization). After 30 days, 200 µl of the above-mentioned mixture was administered intraperitoneally to the mice (second immunization). After 21 days from the second immunization, 200 µl of the PIC solution prepared by diluting the PIC immunogen solution (A 280 nm=0.1) with an equal amount of physiological saline solution was administered intravenously to the mice (final immunization). After 3 days from the final immunization, the spleens were removed aseptically from the mice to use in the following cell fusion.

(c) Cell Fusion

The above-mentioned aseptically removed spleens were placed in a laboratory dish containing 5 ml of DME medium including 15 percent fetal calf serum. Then, about 15 ml of DME medium containing 15 percent fetal calf serum was injected to the spleens for flushing out the spleen cells, then the suspension of the spleen cells was passed through a nylon mesh. The spleen cells were collected in a 50 ml centrifugation tube and were centrifuged at 500×g for 10 minutes. To the resulting pellets, 4 ml of a hemolyzing solution (155 mM-$NH_4Cl$, 10 mM-$KHCO_3$, 1 mM-Na2EDTA;pH 7.0) was added to suspend the pellets. The suspension was allowed to stand at 0° C. for 5 minutes to lyse the red blood cells therein. A DME medium containing 15 percent fetal calf serum was added, then centrifugation was carried out. The resulting pellets were washed with a DME medium by the centrifugation method and the number of living spleen cells was measured.

The above spleen cells ($1 \times 10^8$) were added to about $2 \times 10^7$ precultivated mouse myeloma cells SP2/0-Ag14 (Rikagaku Kenkyusho Gene Bank Cell Bank), and the whole was thoroughly mixed in a DME medium, and centrifuged (500×g, 10 min). The supernatant was sucked up, the pellets were thoroughly unfastened, 0.5 ml of 40 percent polyethylene glycol 4000 solution (warmed at 38° C.) was added dropwise, then the centrifugation tube was gently rotated by hand for 1 minute to thereby mix the polyethylene glycol solution with the cell pellets. Then, a DME medium warmed at 38° C. was added in 1 ml amounts every 30 seconds and the tube was gently rotated. After this procedure was repeated 10 times, 20 ml of a DME medium containing 15 percent fetal calf serum was added and centrifugation was carried out (500×g, 10 min). After the supernatant was removed, the cell pellets were washed twice by the centrifugation method using a HAT medium (prepared by adding, to a DME medium, aminopterin, thymidine and hypoxanthine so that the concentrations thereof become to $4 \times 10^{-7}$M, $1.6 \times 10^{-5}$M, and $1 \times 10^{-4}$M, respectively) containing 15 percent fetal calf serum, then were suspended in 40 ml of the HAT medium. The cell suspension was divided and poured into the wells of 96-well cell cultivation plates in an amount of 200 µl, and the cultivation was started in a carbon dioxide gas incubator including 5 percent carbon dioxide gas at 37° C. During the cultivation, about 100 µl of the medium in each of the wells was removed at two to three day intervals and a new 100 µl amount of HAT medium was added so as to select the hybridomas growing in the HAT medium. From the eighth day, the medium was substituted for a HAT medium (prepared by adding, to a DME medium, thymidine and hypoxanthine so that the concentrations thereof become to $1.6 \times 10^{-5}$M and $1 \times 10^{-4}$M, respectively) containing 15 percent fetal calf serum and the hybridomas were observed. On the tenth day, the hybridomas producing the PIC antibodies were screened by the ELISA method mentioned below.

(d) Establishment of Hybridomas

The presence of produced antibodies in the supernatant of the hybridoma cultivation liquid was determined by the ELISA method. Into the wells of 96-well ELISA plates (Immulon II, Nippon Dynatech K. K.), the PIC immunogen solution (A280 nm=0.05, diluted by physiological saline solution) was distributed in an amount of 50 μl, and allowed to stand at 25° C. for 2 hours. Then, the wells were washed three times by 0.05 percent Tween 20® physiological (pryploxethylene sorbitan monolaurate) saline solution, then 50 μl of the supernatant of the cultivation liquid was added to the wells and a reaction was carried out at 25° C. for 1 hour Tween 20® is a non-ionic detergent.

Then, 50 μl of a peroxidase binding anti-mouse antibody (Dako Co., Denmark) diluted 200-fold by Tween 20®-physiological saline solution were added to the wells. After the reaction was completed, the wells were washed three times by 0.05 percent Tween 20®-physiological saline solution, 250 μl of a solution containing 0.5 mM aminoantipyrine, 10 mM phenol, and 0.005 percent hydrogen peroxide was added to the wells, a reaction was carried out at 25° C. for 30 minutes, and the absorption at 490 nm of the wells was measured. As a result, antibody production was observed in three of the 192 wells. The hybridomas in the three wells were transferred to 24-well plates and were cultivated for 4 to 5 days in a HAT medium containing 15 percent fetal calf serum. Thereafter, the presence of production of anti-PIC antibodies was confirmed by the ELISA method again, then cloning was carried out by the limiting dilution method. In the limiting dilution method, 100 μl of the cell suspension diluted by an HT medium to a concentration of 5 hybridomas/ml was distributed into the wells of 96-well plates wherein $2 \times 10^4$ abdominal cells of normal BALB/C mice were distributed in advance in each well. After 10 days, clones of the hybridoma producing anti-PIC specific antibodies were screened by the ELISA method.

As a result, 20 to 40 clones producing antibodies were obtained for each hybridoma. From these clones, stable ones exhibiting strong proliferation and a high ability for secreting antibodies were selected, and recloned by the same method as above, and three hybridomas PIC-1, PIC-2 and PIC-3 producing anti-PIC antibodies were obtained. The reactivities of the three monoclonal antibodies PIC-1, PIC-2 and PIC-3 secreted from the above three hybridomas with a human plasminogen (Athens Research and Technology, Inc., U.S.) or a human $\alpha_2$-plasmin inhibitor (Athens Research and Technology, Inc., U.S.) were examined by the ELISA method as above, by covering the human plasminogen or human $\alpha_2$-plasmin inhibitor on the 96-well ELISA plates. The monoclonal antibody PIC-1 reacted with the human plasminogen, but did not react with the human $\alpha_2$-plasmin inhibitor. The monoclonal antibody PIC-2 reacted with the 92-plasmin inhibitor, but did not react with the human plasminogen. Further, the monoclonal antibody PIC-3 did not react with the human plasminogen and the human $\alpha_2$-plasmin inhibitor.

The above-mentioned hybridomas were domestically deposited in the Fermentation Research Institute of the Agency of Industrial Science and Technology of the Japanese Ministry of International Trade and Industry (address: 1–3, Higashi 1-chome, Tsukuba-shi, Ibaraki-ken, 305, Japan) on Dec. 4, 1990 and were transferred to international deposition on Dec. 16, 1991. The international deposition numbers (numbers in parentheses following the international deposition numbers are domestic deposition numbers) are FERM BP-3681 (FERM P-11888) for the hybridoma PIC-1, FERM BP-3682 (FERM P-11889) for the hybridoma PIC-2, and FERM BP-3683 (FERM P-11890) for the hybridoma PIC-3.

Example 2

Preparation of Monoclonal Antibodies (a) In vitro Method

Mouse hybridoma PIC-1, PIC-2 and PIC-3 were cultivated respectively in DME media containing 15 percent fetal calf serum at 37° C. for 72 to 96 hours in a 5 percent carbon dioxide atmosphere. After the cultures were centrifuged (10,000×g, 10 minutes), solid ammonium sulfate was gradually added to the supernatants so that a final concentration thereof was 50 percent. The mixtures were agitated for 30 minutes while cooled with ice, then were allowed to stand for 60 minutes and were then centrifuged (10,000×g, 10 minutes). The residues were dissolved in small amounts of a 10 mM phosphate buffer solution (pH 8.0) and were applied to a column of DEAE-cellulose which had been equilibrated by a 1000-fold amount of 10 mM phosphate buffer solution. The monoclonal antibodies were eluted by the density gradient method from a 10 mM phosphate buffer solution (pH 8.0) to a 10 mM phosphate buffer solution (pH 8.0) containing 0.2M-NaCl. The eluted monoclonal antibodies were concentrated by the ultra filtration method and were dialyzed to a 0.01M phosphate buffer solution (pH 8.0). To remove the calf serum IgG, the dialyzed products were passed through goat anti-calf serum IgG-Sepharose 4B columns. Then, the passed solutions were applied to protein A-Sepharose 4B columns equilibrated with a 0.1M phosphate buffer solution (pH 8.0). The columns were eluted by a buffer solution (pH 3.5) to obtain the solution of the purified anti-PIC specific monoclonal antibody PIC-1 and similarly the monoclonal antibody PIC-2 and monoclonal antibody PIC-3.

(b) In Vivo Method

Pristane (2,6,10,14-tetramethylpentadecane) (0.5 ml) was administered intraperitoneally into 10 to 12 week old BALB/c mice. After 14 to 20 days, hybridoma PIC-1, PIC-2, or PIC-3 proliferated in vitro was inoculated into the abdominal cavities of the mice in an amount of $2 \times 10^6$ cells/mouse. About 10 to 15 ml of ascites was obtained from a mouse for each of the hybridomas. The concentrations of the antibodies were 2 to 10 mg/ml. The purification of the monoclonal antibodies from ascites was carried out by the method same as that in vitro purification (however, except the step of passing through a column of goat anti-calf serum IgG-Sepharose).

Example 3

Identification of Immunoglobulin Class and Specificity of Monoclonal Antibodies

The immunoglobulin class and specificity of the anti-PIC specific monoclonal antibodies PIC-1, PIC-2 and PIC-3 were examined by the Ouchterlony immunodiffusion method, the enzyme immunoassay method, and the immunoblotting method, respectively. The results are shown in Table 1.

TABLE 1

| Monoclonal antibody | Immunoglobulin class | Reactivity with human plasminogen | Reactivity with PIC | Reactivity with human $\alpha_2$-plasmin inhibitor | Reactivity with human plasminogen Kringle 2 and 3 | Reactivity with human plasminogen Kringle 1 | Reactivity with human val-plasminogen |
|---|---|---|---|---|---|---|---|
| PIC-1 | $IgG_1$ | + | + | – | Yes | No | No |
| PIC-2 | $IgG_1$ | – | + | + | No | No | No |
| PIC-3 | $IgG_1$ | – | + | – | No | No | No |

In Table 1, "+" indicates that a reaction is observed in the ELISA method, while "–" indicates no reaction is observed in the ELISA method. Further, "yes" indicates that a reaction is observed in the immunoblotting method, while "no" indicates that no reaction is observed in the immunoblotting method.

Example 4
Coating of Insoluble Carrier (Latex) with Antibody

An aqueous solution (2 ml) containing the monoclonal antibody PIC-1 (2.0 mg/ml) and a latex solution (2 ml) (2%, Dow Chemical Co.: particle size=0.482 μm) were mixed together and agitated for about one hour. The mixture was centrifuged (20,000×g, 10 minutes), then the precipitate was suspended in a 0.1 percent BSA solution and agitated for about one hour. The resulting suspension was again centrifuged (20,000×g, 10 minutes), then the precipitate was suspended in water and agitated for about 2 hours. In the above manner, a liquid containing a monoclonal antibody PIC-1/latex complex was obtained. In the same manner, monoclonal antibody PIC-2 or monoclonal antibody PIC-3 was used to prepare liquids containing complexes of the individual monoclonal antibodies and latex.

The complex of the mixture of the monoclonal antibodies with the latex was prepared as follows: Two ml of an aqueous solution containing 0.66 mg/ml of each of the monoclonal antibody PIC-1, PIC-2 and PIC-3 was mixed with 2 ml of a latex solution (2%, Dow Chemical Co., particle size=0.482 μm) and the mixture was agitated for about 1 hour. Thereafter, the mixture was treated in the same manner as above to prepare the monoclonal antibody PIC-1/monoclonal antibody PIC-2/monoclonal antibody PIC-3/latex complex.

The same procedure was repeated, except that an aqueous solution containing 1 mg/ml of each of the monoclonal antibody PIC-1 and monoclonal antibody PIC-2 was mixed in an equal amount of a latex solution, to prepare a monoclonal antibody PIC-1/monoclonal antibody PIC-2/latex complex.

Example 5
Assay by Slide Agglutination Reaction

Forty μl of the antibody-latex-complex containing solution prepared in Example 4 and 40 μl of aqueous solutions containing various concentrations of PIC were mixed on a glass slide and rocked. After 3 minutes, the agglutination was examined visually. The results are shown in Table 2.

In Table 2, "+" means that there is agglutination, while "–" means that there is no agglutination. Further, in the column of the antibody/latex complex in Table 2, the type of the complex is expressed by the monoclonal antibody bonding with the complex. Therefore, for example, PIC-1 means a monoclonal antibody PIC-1/latex complex, and PIC-1+PIC-2 means a mixture of an equal amounts of a monoclonal antibody PIC-1/latex complex and a monoclonal antibody PIC-2/latex complex. Further, PIC-1/PIC-2 means a monoclonal antibody PIC-1/monoclonal antibody PIC-2/latex complex.

TABLE 2

| Type of monoclonal antibody/latex complex | PIC concentration (μg/ml) | | | | | | | | | | |
|---|---|---|---|---|---|---|---|---|---|---|---|
| | 256–512 | 128–256 | 64–128 | 32–64 | 16–32 | 8–16 | 4–8 | 2–4 | 1–2 | 1–0.5 | 0.5–0.25 |
| PIC-1 | – | – | – | – | – | – | – | – | – | – | – |
| PIC-2 | – | – | – | – | – | – | – | – | – | – | – |
| PIC-3 | – | – | – | – | – | – | – | – | – | – | – |
| PIC-1 + PIC-2 | + | + | + | + | + | + | + | + | + | + | – |
| PIC-1/PIC-2 | + | + | + | + | + | + | + | + | + | + | – |
| PIC-1 + PIC-2 + PIC-3 | + | + | + | + | + | + | + | + | + | + | – |
| PIC-1/PIC-2/PIC-3 | + | + | + | + | + | + | + | + | + | + | – |

Example 6
Recovery Test of Purified PIC

The concentration of PIC in five specimens (plasma from healthy person A, healthy person B, DIC patient C, DIC patient D, DIC patient E) were measured using the monoclonal antibody PIC-1/monoclonal antibody PIC-2/latex complexed solution of Example 5. Then, 2 μg/ml, 4 μg/ml, and 8 μg/ml of purified PIC were added to the specimens and recovery tests were carried out. The measurement values were obtained semiquantitatively from the number of dilutions of the specimen eliminating the agglutination.

TABLE 3

| Specimen | Am't of PIC measured (μg/ml) | Am't of PIC added (μg/ml) | Measurement value after addition |
|---|---|---|---|
| A | <1 | 2 | 2–4 |
|   |    | 4 | 4–8 |
|   |    | 8 | 8–16 |
| B | <1 | 2 | 2–4 |
|   |    | 4 | 4–8 |

TABLE 3-continued

| Specimen | Am't of PIC measured (μg/ml) | Am't of PIC added (μg/ml) | Measurement value after addition |
|---|---|---|---|
|   |   | 8 | 8–16 |
| C | 1–2 | 2 | 2–4 |
|   |   | 4 | 4–8 |
|   |   | 8 | 8–16 |
| D | 4–8 | 2 | 4–8 |
|   |   | 4 | 8–16 |
|   |   | 8 | 8–16 |
| E | 8–16 | 2 | 8–16 |
|   |   | 4 | 8–16 |
|   |   | 8 | 16–32 |

Example 7
PIC Values of Healthy Persons and DIC Patients

The monoclonal antibody PIC-1/monoclonal antibody PIC-2/latex complex solution used in Example 6 was used to measure th amounts of PIC of 12 specimens of the plasma from healthy persons and 15 specimens of the plasma from DIC patients. The results are shown in FIG. 1. The amount of PIC of the healthy persons was less than 1 μg/ml in all cases. To the contrary, the value for the DIC patients was over 2 μgml in all cases.

Applicability in Industry

As explained above in detail, according to the present invention, it is possible to specifically and simply measure the amount of PIC in the plasma of patients by the agglutination method without diluting the plasma specimen and without suffering from interference of the free plasminogens and free $\alpha_2$-plasmin inhibitor in the plasma. This is made possible for the first time by the present invention. Therefore, the present invention provides a means useful for the diagnosis of DIC or the like and pathological research.

We claim:

1. A monoclonal antibody which specifically binds to human plasmin-α2-plasmin inhibitor complex and human plasminogen within a region of plasminogen containing Kringle 2 and Kringle 3, but does not bind to human α2-plasmin inhibitor or human plasminogen Kringle 1.

2. A hybridoma or cell line thereof, which secretes the monoclonal antibody according to claim 1.

3. A monoclonal antibody which specifically binds to human plasmin-α2-plasmin inhibitor complex and human plasminogen within a region of plasminogen containing Kringle 2 and Kringle 3, but does not bind to human α2-plasmin inhibitor or human plasminogen Kringle 1, wherein said monoclonal antibody is produced by the hybridoma deposited under International Deposit No. FERM BP-3681.

4. A hybridoma deposited under International Deposit No. FERM BP-3681, or cell line thereof, which secretes the monoclonal antibody according to claim 3.

5. A monoclonal antibody which specifically binds to human plasmin-α2-plasmin inhibitor complex and human α2-plasmin inhibitor, but does not bind to human plasminogen, wherein said monoclonal antibody is produced by the hybridoma deposited under International Deposit No. FERM BP-3682.

6. A hybridoma deposited under International Deposit No. FERM BP-3682, or cell line thereof, which secretes the monoclonal antibody according to claim 5.

7. A monoclonal antibody which specifically binds to human plasmin-α2-plasmin inhibitor complex, but does not bind to human plasminogen or human α2-plasmin inhibitor, wherein said monoclonal antibody is produced by the hybridoma deposited under International Deposit No. FERM BP-3683.

8. A hybridoma deposited under International Deposit No. FERM BP-3683, or cell line thereof which secretes the monoclonal antibody according to claim 7.

9. A method for quantitating an amount of human plasmin-α2-plasmin inhibitor complex in an assay sample comprising human plasmin-α2-plasmin inhibitor complex, human plasminogen and α2-plasmin inhibitor, said method comprising the steps of:

(1) contacting the assay sample with a monoclonal antibody (A) and at least one of a monoclonal antibody (B) and a monoclonal antibody (C); and (2) detecting and correlating an agglutination reaction in the assay sample to an agglutination reaction in a standard measurement to thereby quantitate the amount of human plasmin-α2-plasmin inhibitor complex in the sample, wherein:

(a) said monoclonal antibodies are immobilized on the same insoluble particulate carrier or on different insoluble particulate carriers;

(b) the monoclonal antibody (A) specifically binds to the human plasmin-α2-plasmin inhibitor complex and human plasminogen within a region of plasminogen containing Kringle 2 and Kringle 3, but does not bind to human α2-plasmin inhibitor or human plasminogen Kringle 1;

(c) the monoclonal antibody (B) specifically binds to human plasmin-α2-plasmin inhibitor complex and human α2-plasmin inhibitor, but does not bind to human plasminogen; and (d) the monoclonal antibody (C) specifically binds to human plasmin-α2-plasmin inhibitor complex, but does not bind to human plasminogen or human α2-plasmin inhibitor.

10. The method according to claim 9, wherein said monoclonal antibody (A) is produced by the hybridoma deposited under International Deposit No. FERM BP-3681, or a cell line thereof.

11. The method according to claim 9, wherein the assay sample is contacted with monoclonal antibody (B), which is produced by the hybridoma deposited under International Deposit No. FERM BP-3682, or a cell line thereof.

12. The method according to claim 11, wherein said monoclonal antibody (A) is produced by the hybridoma deposited under International Deposit No. FERM BP-3681, or a cell line thereof.

13. The method according to claim 12, wherein the assay sample is additionally contacted with monoclonal antibody (C), which is produced by the hybridoma deposited under International Deposit No. FERM BP-3683, or a cell line thereof.

14. The method according to claim 11, wherein the assay sample is additionally contacted with monoclonal antibody (C), which is produced by the hybridoma deposited under International Deposit No. FERM BP-3683, or a cell line thereof.

15. The method according to claim 9, wherein the assay sample is contacted with monoclonal antibody (C), which is produced by the hybridoma deposited under International Deposit No. FERM BP-3683, or a cell line thereof.

16. The method according to claim 15, wherein said monoclonal antibody (A) is produced by the hybridoma deposited under International Deposit No. FERM BP-3681, or a cell line thereof.

17. The method according to claim 9, wherein said assay sample is a body fluid.

18. The method according to claim 17, wherein said body fluid is plasma.

19. The method according to claim 18, wherein said plasma is undiluted.

20. The method according to claim 19, wherein said same insoluble particulate carrier or said different insoluble particulate carriers comprise latex particles.

21. The method according to claim 9, wherein said same insoluble particulate carrier or said different insoluble particulate carriers comprise latex particles.

22. The method according to claim 9, wherein said assay sample is contacted with monoclonal antibodies (A) and (B) immobilized on the same insoluble particulate carrier.

23. The method according to claim 9, wherein said assay sample is contacted with monoclonal antibodies (A) and (B) immobilized on different insoluble particulate carriers.

24. The method according to claim 9, wherein said assay sample is contacted with monoclonal antibodies (A) and (C) immobilized on the same insoluble particulate carrier.

25. The method according to claim 9, wherein said assay sample is contacted with monoclonal antibodies (A) and (C) immobilized on different insoluble particulate carriers.

26. The method according to claim 9, wherein said assay sample is contacted with monoclonal antibodies (A), (B), and (C), each immobilized on the same insoluble particulate carrier.

27. The method according to claim 9, wherein the assay sample is contacted with monoclonal antibodies (A), (B), and (C) each immobilized on different insoluble particulate carriers.

28. The method according to claim 9, wherein the assay sample is contacted with monoclonal antibodies (A) and (B) immobilized on the same insoluble particulate carrier and monoclonal antibody (C) immobilized on a different insoluble particulate carrier.

29. The method according to claim 9, wherein the assay sample is contacted with monoclonal antibodies (A) and (C) immobilized on the same insoluble particulate carrier and monoclonal antibody (B) immobilized on a different insoluble particulate carrier.

* * * * *